United States Patent [19]

Weber et al.

[11] Patent Number: 4,619,612
[45] Date of Patent: Oct. 28, 1986

[54] DENTAL SPRAY HANDPIECE

[75] Inventors: Walter Weber, Lorsch; Doris Frank-Voeglein, Zwingenberg, both of Fed. Rep. of Germany

[73] Assignee: Siemens Aktiengesellschaft, Berlin & Munich, Fed. Rep. of Germany

[21] Appl. No.: 660,118

[22] Filed: Oct. 12, 1984

[30] Foreign Application Priority Data

Oct. 12, 1983 [DE] Fed. Rep. of Germany ....... 3337166

[51] Int. Cl.⁴ .............................................. A61C 17/00
[52] U.S. Cl. ........................................ 433/80; 433/29
[58] Field of Search .................................... 433/80, 29

[56] References Cited

U.S. PATENT DOCUMENTS

| | | |
|---|---|---|
| 1,989,162 | 1/1935 | Barr ......................................... 433/80 |
| 2,522,261 | 9/1950 | Freedman . |
| 3,614,415 | 10/1971 | Edelman . |
| 3,698,088 | 10/1972 | Austin ................................... 433/80 |
| 4,149,315 | 4/1969 | Page, Jr. et al. . |

Primary Examiner—Robert Peshock
Attorney, Agent, or Firm—Hill, Van Santen, Steadman & Simpson

[57] ABSTRACT

The present invention is directed to a dental spray handpiece for agents such as air and water having a nozzle member with a discharge orifice at one end and a connecting element at the other end and a housing forming a grip piece for the dental handpiece containing an arrangement for controlling flow of the agents and a connection to a supply hose with the nozzle and having a coacting element forming a rotary joint characterized by the nozzle member having a light conductor extending from the discharge orifice up to the rotary joint and a light source being provided in the vicinity of the rotary joint and in optical communication with the other end of the light conductor so that light is conducted through the nozzle and projected out of the nozzle adjacent to the discharge opening.

20 Claims, 18 Drawing Figures

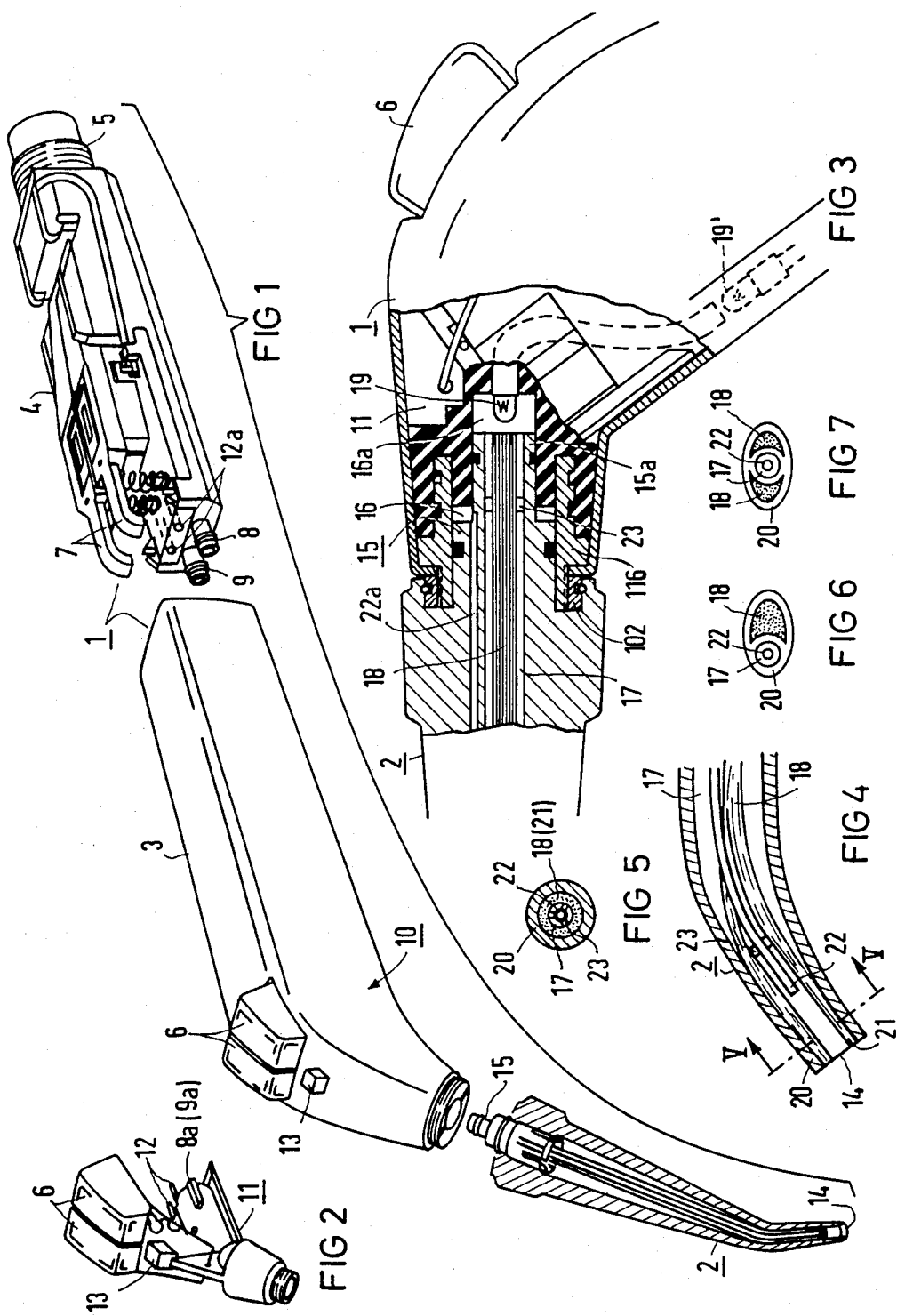

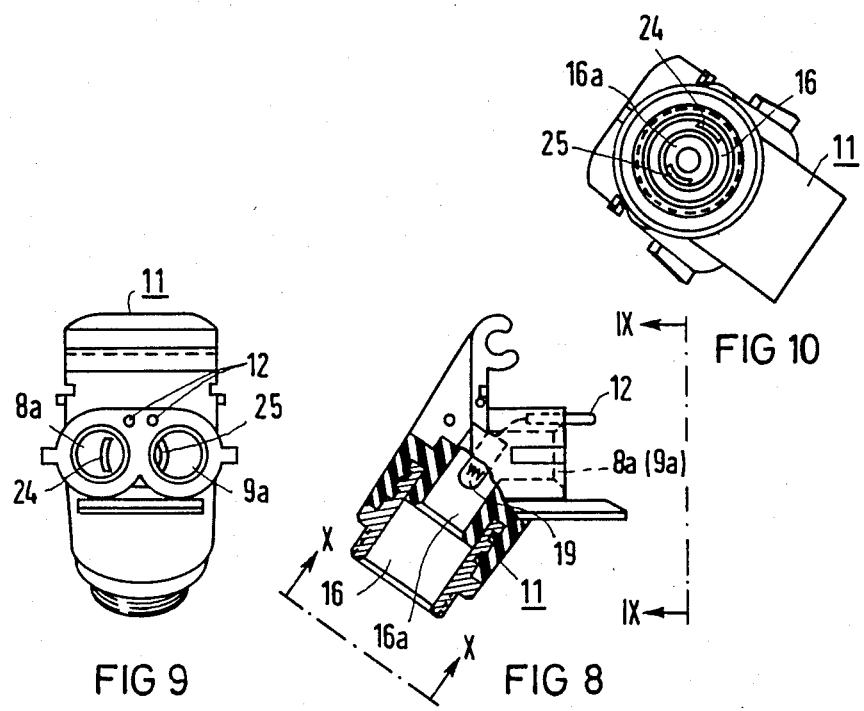
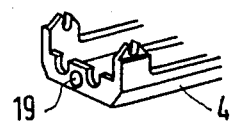
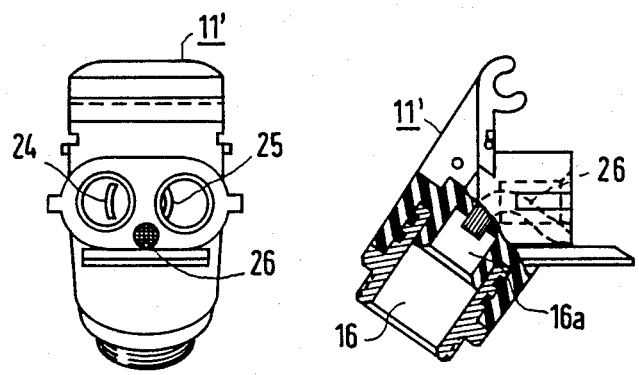
FIG 10
FIG 9    FIG 8
FIG 11
FIG 12    FIG 13

DENTAL SPRAY HANDPIECE

BACKGROUND OF THE INVENTION

The present invention is directed to a dental spray handpiece having an elongated nozzle with a discharge orifice through which air, water or a mixture thereof is sprayed. The dental handpiece has a housing forming a grip or grasping member which at one end is connected to a supply hose and has the other end connected to the nozzle by a rotating joint which allows disassembly. The handpiece also includes an arrangement for conducting light from a source to a point adjacent the discharge orifice where the light is projected in the direction of the spray discharge.

Spray handpieces or dental syringes which have a nozzle connected to a housing and are provided with a valve arrangement to enable either discharging air or water or a mixture of the two, are known. An example of the handpiece is disclosed in U.S. Pat. No. 4,149,315.

In order to have a better view of the work area in the region of the oral cavity when using a spray handpiece having a spray nozzle part, it has been necessary up to now to provide an additional handpiece with an illuminating means, for example, in the form of a light waveguide handpiece which is known, for instance, from U.S. Pat. No. 3,614,415. Certain locations in the oral cavity, either cannot be illuminated or cannot be satisfactorily illuminated with normal work area lamps because heavy shadows will occur under certain conditions at the immediate treatment location when working with the instrument or because the light intensity is inadequate for adequately illuminating the oral cavity. These locations can be optimally illuminated with such a punctiform illumination device as disclosed in the above patent.

A dental handpiece equipped with an illumination device is disclosed in U.S. Pat. No. 2,522,261. This handpiece indeed is designed for the emission of water and air but is principally designed for sucking fluid out of the oral cavity of the patient. Accordingly, the handpiece essentially consists of a central suction tube leading up to the suction mouthpiece which is connected to a handle portion by an angled tube portion so that the arrangement has a hook or U-shaped configuration. The delivery of air and water will occur by means of feed lines which are secured to the outside of this suction tube.

The illumination means, which consist of a lamp is disposed at a horizontal part on the inside of the angled suction tube, which is connected to the evacuation means. The lamp is supplied with voltage by means of electrical lines conducted in the suction channel or tube and is interchangeably mounted in a correspondingly designed mount. The evacuation handpiece can be pivoted toward both sides together with the lamp and the ends of the agent lines. The disadvantage is that the agent lines including those on the outside of the tube are twisted on their axes during this pivoting of the mouthpiece of the handpiece and the cross-section is thus constricted with the agent delivery being thereby interrupted under certain conditions.

SUMMARY OF THE INVENTION

The present invention is to provide a dental spray handpiece which has improved utility and provides for both the illumination and the emission of spray agents to such an effect that no separate illumination instrument is necessary for illuminating and viewing the treatment location during or, respectively, immediately after employment of the sprayer. These measures are provided without any deleterious effect on the external shape of the spray handpiece, for example, without any parts attached to the spray nozzle and thus hanging down or, respectively, projecting therefrom. In addition, the twisting of agent lines as mentioned above is likewise avoided.

In order to accomplish these objects, the present invention is directed to an improvement in a dental spray handpiece for spraying agent, the handpiece including a nozzle member having a discharge orifice at one end and a housing forming a grip piece for the dental handpiece with one end having means for forming a connection with the supply hose, said nozzle at a second end and the housing at its second end each having coacting elements forming joint means for releasably connecting the nozzle on the housing with rotatable movement therebetween. The improvement comprises a light source being disposed in the handpiece adjacent the joint means and a light conductor being centrally disposed in the nozzle and extending from a point adjacent the discharge orifice up to the joint means for receiving light from said source when the nozzle is connected on the housing by said joint means.

The improvements of the present invention enable integrated illumination means to be advantageously designed so that the light-emitting element, preferably an incandescent electrical bulb, is disposed in the grasping or grip member of the spray handpiece and a light conductor, preferably a bundle of fiber optical light waveguides, is disposed as the light forwarding or conducting element in the removably mounted nozzle. Thus, one end of the light conductor terminates with the end of the nozzle and its other end is arranged centrally in a center spigot or channel and is positioned opposite the light supplying element which is mounted adjacent the grip member. The light source has a lamp mount which is preferably interchangeably constructed and is designed in particular so that the spray handpiece without or respectively with the illumination means can be optionally provided at the factory or even subsequently by means of merely omitting or respectively attaching the lamp mount part without having a negative influence on the flow of the agents. To this end, the lamp mount is designed as an easily interchangeable insert preferably in the form of a cartridge.

The course of the light conduit in the nozzle of the spray handpiece can advantageously terminate with the conductor being a concentric ring to the air and water discharge openings at the discharge orifice or aperture. It is also possible for the light connductor adjacent the discharge orifice or opening to assume other shapes such as of a half-moon shape or to form two or more crescent-shaped, round or other shaped sections which are disposed about the discharge opening or orifice of the nozzle.

While the elements of the nozzle and of the housing which form the joint means comprise a cylindrical socket receiving a hollow cylindrical pin or peg which can be either arranged with the cylindrical peg being on the nozzle or on the housing, a particular advantage can be achieved when the lamp is disposed in the end face of the cavity of the socket into which the guide peg or cylindrical hollow pin of the nozzle is engaged. When the air feed from the grip member also discharges freely into this cavity, the lamp will receive adequate cooling on the one hand to increase its service life and on the other hand the air is slightly warmed by passing over the lamp. The light supplying element is advantageously disposed in a transitional piece which produces a transition from the straight housing arrangement to an angle part of the handpiece. This transition piece can be easily disconnected by means of a plug-type connection from the valve arrangement or housing for the fluid agents as well as with respect to electrical contacts so that the transition piece can be designed as an inexpensive-to-manufacture part. Thus, it is conceivable that the lamp can be rigidly disposed in this transition piece and the entire piece be simply replaced when the lamp malfunctions or burns out.

Alternatively, disposition of the lamp in the transition piece can also be provided in the nozzle or back in the valve housing with the valves for the various agents. When the lamp is disposed in the nozzle, and is mounted to rotate therewith, the power supply to the lamp is ensured by utilizing slip rings. When the lamp is disposed in the housing adjacent the valves, light transmission through the transition piece will occur by means of a correspondingly designed light conductor which terminates in the cavity of the joint means. Switching the lamp on and off can be advantageously undertaken by means of a switch or key which is disposed in the immediate proximity of the switches or actuation elements for the water and air. When this switch or, respectively, the key, is seated preceding the actuation elements for both the air and water, the light can be easily switched with the thumb both separately from as well as together with the spray agents which are the air and water or mixtures thereof.

BRIEF DESCRIPTION OF THE DRAWINGS

FIG. 1 is an exploded perspective view with portions in cross-section for purposes of illustration of the spray handpiece in accordance with the present invention;

FIG. 2 is a perspective view of a transition piece of the spray handpiece without the external housing;

FIG. 3 is an enlarged partial side view of the handpiece with portions broken away for purposes of illustration to show the transition piece and the joint between the transition piece and the nozzle;

FIG. 4 is an enlarged partial cross-sectional view of the discharge end of the nozzle;

FIG. 5 is a cross-sectional view taken along the lines V—V of FIG. 4;

FIG. 6 is an end view of a modification of the discharge orifice of the nozzle of the present invention;

FIG. 7 is an end view of another modification of the discharge orifice of the nozzle of the present invention;

FIG. 8 is a side view with portions broken away for purposes of illustration of a transition piece in accordance with the present invention;

FIG. 9 is an end view taken from line IX—IX of FIG. 8;

FIG. 10 is an end view taken from line X—X of FIG. 8;

FIG. 11 is a partial perspective view of a modification of a valve housing in accordance with the present invention;

FIG. 12 is an end view similar to FIG. 9 of a modification of a transition piece utilized with the valve housing of FIG. 11;

FIG. 13 is a side view of the valve housing of FIG. 12 with portions broken away for purposes of illustration;

DESCRIPTION OF THE PREFERRED EMBODIMENTS

Figure 14:
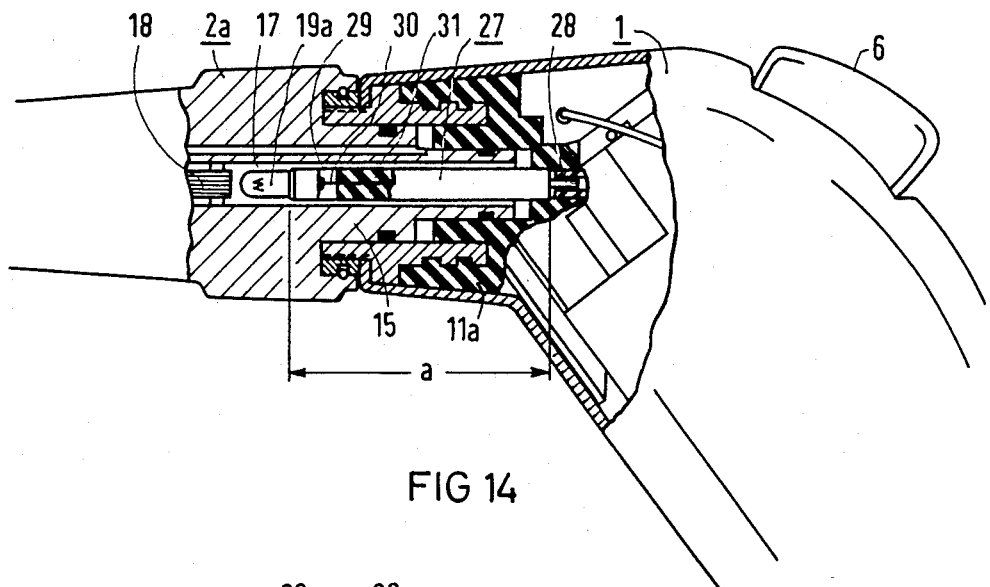
FIG. 14 is an enlarged side view with portions broken away for purposes of illustration of an embodiment of the dental spray handpiece in accordance with the present invention.

The spray handpiece 1 consists of a housing 3, which at one end is connected to a nozzle 2 by a joint means that enables relative rotation between the housing 1 and the nozzle and also an easy release of the nozzle from the housing. The housing 1 acts as a grip or grasping piece or member and receives a valve housing or arrangement 4 which has one end provided with a connection 5 for a supply hose (not illustrated). The valve arrangement 4 contains valves which are not shown in detail for controlling the flow of the agents such as water and air and also contains electrical heating elements for heating the agents. The actuation of the valves and the switches for the heaters occurs by means of pressing buttons 6 which actuate transmission levers 7 of the valve arrangement 4. With pivotal movement of the levers 7, the valves are switched on and electrical contacts are made. The feed of the agents such as air and water will then occur in a known manner via lines whose ends terminate in hollow prongs or tubular pins 8 and 9.

The housing 3 at an end opposite the connection 5 has a bent or angled area generally indicated by the arrow 10. This arrow or region forms a transition from the straight part of the housing 3 to the angled part. A transition piece 11 (FIG. 2) is received in the transition region 10 and is provided with bores or sockets 8a and 9a which receive the hollow pins or prongs 8 and 9, respectively, when the valve arrangement or housing 4 is received in the housing 3. In addition, the transition piece has electrical prongs 12 which are received in electrical sockets 12a of the housing 4 for supplying electrical energy to a lamp which is disposed inside of the transition member or piece 11. As illustrated, the transition piece 11 also has a switch 13, which enables switching the lamp on and off. The switch 13 is arranged immediately next to the keys 6 for the air and water and as illustrated is positioned in the direction toward the nozzle which enables good actuation thereof.

The nozzle 2 at an end opposite a discharge orifice 14 is provided with an element such as a cylindrical hollow plug, prong or peg 15 that has a stepped configuration with a large diameter portion and a small diameter portion 15a (see FIG. 3). Each of the portions is provided with an O-ring in a known manner and coact with corresponding sockets 16 and 16a which are in the transition member 11 to form the joint means. Due to provision of the O-rings, a water and air-tight seal is formed between each of the cylindrical portions 15 and 15a and the respective sockets 16 and 16a.

As illustrated in FIG. 3, the large diameter portion 15 is received in the socket 16 and the small diameter portion 15a is received in the small diameter socket 16a. The prong 15a which extends in the section 16a has a channel 17 at its center for the passage of air. As illustrated, a light conductor 18 is disposed in this channel. The cross-section of the channel 17 is constructed to be appropriately large so that an adequate amount of air can be conducted to the nozzle orifice 14 despite the insertion of the light conductor 18 which is illustrated as being a bundle of optical fibers. The light conductor 18 is advantageously supported in the channel 17 by means of webs or spacers such as 23. A lamp 19 is disposed in the transition element and centrally arranged so that its light will be received by the end of the light conductor 18. It is also possible to position the lamp in the valve housing as indicated by a lamp 19' in broken lines and this arrangement will be discussed in greater detail hereinafter.

As illustrated, transition piece or element 11 has a sleeve 116 which forms part of the cavity or socket 16. In addition, the sleeve 116 extends past the housing 3 and receives an annular member or ring 102 of the nozzle 2. If desired, an appropriate thread arrangement between the sleeve 102 and 116 or a bayonet-type joint can be provided. The sleeve 102 can be constructed to be rotated relative to the nozzle 2 so that easy rotation of the nozzle can be accomplished.

The nozzle, as best illustrated in FIG. 4, at a discharge orifice 14, has the fibers of the waveguide bundle 18 arranged to extend concentrically around the discharge opening which also has a tube 22 arranged on the axis of the opening. The tube 22 extends in the passage or channel 17 to a point where it merges with a second channel 22a that extends to the large diameter socket 16 in the member 11 (see FIG. 3). As illustrated in FIG. 4, the tube 22 terminates at a point set back from the end of the nozzle orifice 14. Thus, water and air being carried through the nozzle will mix and be discharged through the opening.

Instead of having the light conductor arranged to be concentric at the discharge end, it can be disposed adjacent one side as illustrated in the embodiment of FIG. 6. It is also possible to break up the light conductor into two batches which have a crescent or half-moon shape and are disposed on opposite sides of the air channel 17 and the water channel 22 as illustrated in FIG. 7. In both embodiments of FIGS. 6 and 7, the nozzle has an oval configuration. In addition to the shape illustrated in FIGS. 5 6 and 7, the ends of the light conductors can be designed in other shapes such as two or more circles. The arrangement illustrated in FIG. 7 with two groups of conductors has the advantage that the shadows in the work area will be eliminated due to illumination from both sides. Thus, if one side is blocked, for example, by the mirror or the like, illuminations will still occur from the other side.

In the transition piece 11, as best illustrated in FIGS. 8, 9 and 10, the lamp 19 is disposed in the cavity of the small socket 16a. The cavity of the socket 16a is connected by a slot 24 (FIGS. 9 and 10) with the socket or bore 8a into which the prong of the line 8 for the valve arrangement is received. The air coming via the line 8 is thus conducted via the slot 24 into the cavity of the small socket 16a where it is freely discharged. In a similar arrangement, water transfer is obtained by a slot 25 which extends into the cavity of the large socket 16 and is connected to the bore 9a. As also illustrated in the drawings, contact pins or prongs 12 extend parallel to the bores or sockets 8a and 9a and accordingly parallel to the ends 8 and 9 for the air and water. These prongs 12 are received in sockets 12a which are shown in FIG. 1.

An alternative solution or embodiment for the arrangement has the lamp 19', which is indicated in broken lines in FIG. 3, being disposed in the valve arrangement housing 4. With such an arrangement, the valve arrangement will have its housing portions modified so that the light transmission lamp 19' is positioned between the two lines 8 and 9 (FIG. 11). To conduct the light from the lamp 19' which is in the valve housing 4 to the end of the light conductor 18 of the nozzle, a transition piece or member 11' of FIGS. 12 and 13 has a short light conductor formed by a bundle of fibers 26. These are arranged to extend from a position on the end surface to be aligned with the lamp 19' when assembled with the valve arrangement 4 and conduct the light into the cavity 16a to be in alignment with the end of the fiber bundle 18.

Figure 15:
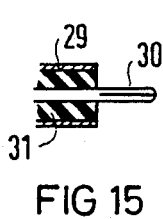
FIG. 15 is an enlarged partial cross-sectional view of a plug arrangement.
Figure 16:
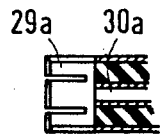
FIG. 16 is a partial cross-sectional view of a socket arrangement of the device of FIG. 14.
Figure 17:
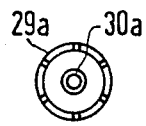
FIG. 17 is an end view of the socket of FIG. 16.

In another embodiment of the device, which is illustrated in FIGS. 14–17, the bulb or lamp 19a is releasably held in a socket 28 of the transmission member 11a by means of a mount 27. The mount 27 consists of an elongated tube 29 of an electrical conductive material which is connected to one pole of the lamp 19a. The mount also has a centrally disposed contact pin 30 which is connected to the other pole of the lamp 19a and is insulated from the tube 29 by an insulating mass 31. As illustrated in FIG. 14, the mount 27 has a length a which is dimensioned so that the lamp 19a extends relatively deep into the passage or channel 17 of the cylindrical peg or prong of a nozzle 2a. To form the connection, the contact pin 30, as illustrated in FIG. 15, extends beyond the end of the tube and is expediently constructed to form a resilient connection with a socket 30a (FIG. 16). The overall socket 28 includes the socket 30a as well as an outer tubular socket 29a which is provided with longitudinal slots so as to resiliently engage the sleeve or tube 29 as the end of the pin 30 is received in the socket 30a.

As illustrated, the socket 28 of the transition member 11a is constructed so that the mount 27 and the lamp 19a are rigidly mounted in the transition piece 11a and thus in the grip piece of the handpiece 1. It is conceivable that the mount 27 can be supported in the air channel 17 of the nozzle with the assistance of elastic rings or supports provided with passages for the passage of air with the frictional force generated by the elastic rings being slightly greater than the pinching force of the socket 28 so that the mount 27 with the lamp 19a will remain in the channel 17 of the nozzle 2a when the nozzle is removed from the grasping or grip piece. A replacement lamp can be subsequently obtained by means of axial movement of the entire holder 27 from the air channel such as 17.

Figure 18:
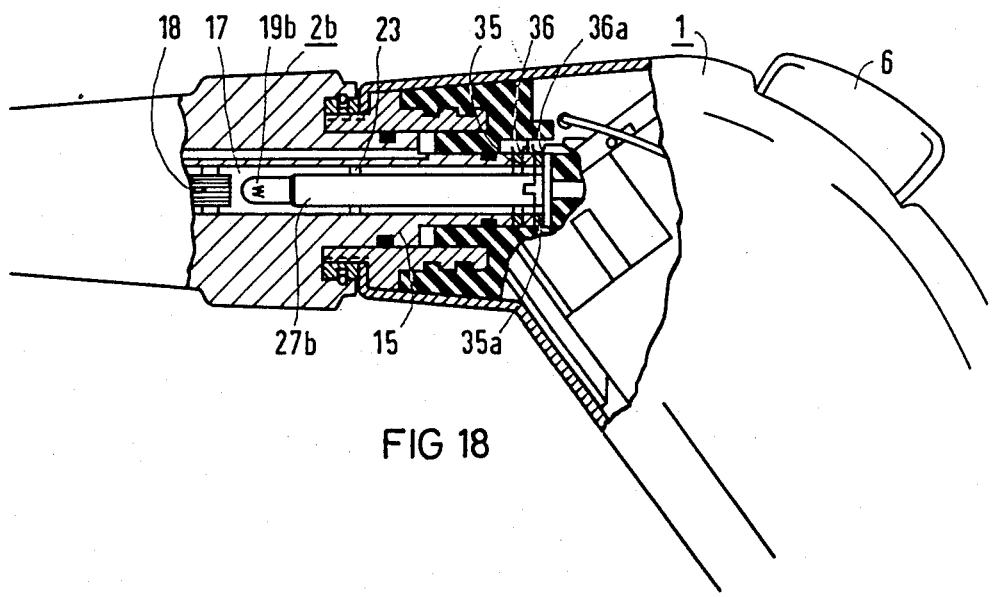
FIG. 18 is an enlarged side view with portions broken away for purposes of illustration of a further embodiment of the dental spray handpiece which is illustrated in FIG. 1.

In another embodiment of the apparatus, lamp 19b on a mount 27b is firmly connected to the nozzle 2b as illustrated in FIG. 18. In this embodiment, the lamp 19b will rotate with the nozzle 2b and the nozzle 2b is provided with slip rings 35 and 35a which are connected to the two electrical conductors of the mount 27b. Contact with the slip rings is made by springs 36 and 36a which press against these and transfer electrical energy to the lamp 19b. As mentioned herein, the lamp 19b and its mount 27b thus rotate with the nozzle 2b whereas in the previous embodiment such as illustrated in FIG. 14 and FIG. 3, the lamp was mounted for non-rotation realtive to the respective transition pieces 11 and 11a.

In each of the embodiments, the connecting elements which form the joint means had the socket provided in the transition piece with the cylindrical prong or peg being disposed on the nozzle part such as the nozzle 2. It is within the invention to reverse this so that the transition piece is provided with the cylindrical projection or peg and the nozzle is provided with the stepped cavities to form the socket. In such an arrangement, the lamp is then preferably mounted on the center of the peg. This arrangement has the advantage of providing a particularly good accessibility to the lamp. The lamp holder can advantageously be already structurally designed such that given an otherwise identical design of the remaining handpiece parts, a spray handpiece with or, respectively, without light transmission can be alternately provided without deterioration of the agent flow merely by means of either inserting or omitting the lamp holder. This is accomplished namely either in the factory or subsequently in the field should a customer so desire. To this end, for example, the lamp 19 can be mounted in the nozzle or in the grip piece in the manner of a cartridge. That part of the nozzle or, respectively, of the grip piece which accepts the lamp holder is structurally prepared to such a degree that the illumination means becomes operative upon insertion of the lamp holder.

Although various minor modifications may be suggested by those versed in the art, it should be understood that we wish to embody within the scope of the patent granted hereon, all such modifications as reasonably and properly come within the scope of our contribution to the art.

We claim:

1. A dental spray handpiece for spraying an agent, the handpiece including a nozzle, a light source, a light conductor and a housing forming a grip piece for the dental handpiece, said nozzle at one end having a discharge orifice, said housing at one end having means for forming a connection with a supply line, said nozzle at a second end and the housing at a second end each having coacting connecting elements forming joint means for releasably connecting the nozzle and the housing together with rotational movement therebetween, said light source being provided in the handpiece adjacent to the joint means and said light conductor being centrally disposed in the nozzle and extending from adjacent the discharge orifice at the one end of the nozzle up to the joint means at the second end of the nozzle for receiving light from said light source.

2. A dental spray handpiece according to claim 1, wherein the light conductor disposed in the nozzle is disposed in a channel of the nozzle for passage of one of the fluid agents in a spaced relationship by spacers.

3. A dental spray handpiece according to claim 2, wherein the light conductor disposed in said nozzle is designed to provide a circular cross-section at the end face located at the joint means and changes to an annular ring configuration at the other end with the annular ring surrounding the discharge orifice for the agents.

4. A dental spray handpiece according to claim 3, wherein the channel receiving the light conductor is a channel for air and the light conductor terminates approximately flush with the plane of the discharge orifice for the air, said second agent being a water channel positioned by spacers in the air channel to terminate at a point set back relative to the discharge orifice for the air channel so that the channel for the water is on the axis of the channel for the air.

5. A dental spray handpiece according to claim 2, wherein the end of the light conductor at the discharge orifice is designed in a shape matched to the cross-section of the discharge orifice for the agents.

6. A dental spray handpiece according to claim 2, wherein at the discharge orifice, the light conductor is divided into two light conducting groups lying diametrically opposite one another with the agents discharge orifice disposed therebetween.

7. A dental spray handpiece according to claim 1, wherein the connecting element of the nozzle is a hollow cylindrical prong having a large diameter portion and a stepped smaller diameter portion with each of the portions being provided with seals, and wherein the connecting element of the housing is a stepped socket having a corresponding large diameter socket and a small diameter socket which correspond to the diameters of the prong and sealingly receiving the prong to form the joint means, said housing having an air channel discharging into the small diameter socket to be conveyed out of a centrally disposed passage in the nozzle, and said centrally disposed light conductor being arranged in said passage for receiving light from the socket.

8. A dental spray handpiece according to claim 7, wherein the housing includes a transition piece containing said large and small diameter sockets of the connecting element for the housing, said transition piece having a portion adjacent the sockets for connecting to the nozzle and a second portion extending at an angle for connecting to the housing, said light source being disposed in the transition piece at the base of the small diameter cavity of the small diameter socket, said transition piece having two plug-type connecting parts for receiving air and water from a valve arrangement in the housing.

9. A dental spray handpiece according to claim 8, wherein the light source is a lamp mounted in the bottom of the small diameter cavity, said transition piece having a pair of plug contacts extending parallel and adjacent to the two plug-type connecting parts for forming electrical connection with the valve arrangement.

10. A dental spray handpiece according to claim 9, wherein the lamp is interchangeably mounted in the transition piece.

11. A dental spray handpiece according to claim 8, wherein the light source is a lamp supported on a holder extending into the cavity of the large and small diameter sockets and into a centrally disposed channel of the nozzle, said holder being releasably held in the transition piece by a plug-type connection which provide a electrical connection for the lamp.

12. A dental spray handpiece according to claim 11, wherein said holder comprises an elongated contact pin, a concentrically arranged tube of electrically conductive material separated from said pin by a layer of insulating material, said tube and pin at one end being connected to different poles of the lamp and said pin extending past the end of the tube at the other end to form part of a plug-type connection, the other part of said plug-type connection being a socket for receiving the pin and a resilient sleeve socket for grasping the outer portion of the tube so that the holder can be removed from the transition piece.

13. A dental spray handpiece according to claim 1, wherein the housing includes a transition piece and a valve arrangement housing, said transition piece having one end provided with plug-type connecting parts to form a connection with agent lines of the valve arrangement housing, the other end of the transition piece having a connecting element of the joint means comprising a first large diameter socket and a small diameter socket, said nozzle having a connecting element of the joint means comprising a large diameter prong and a stepped-down reduced diameter prong having dimensions corresponding to the dimensions of said large and small diameter sockets, said transition member having an intermediate light conductor extending from a center of the small diameter socket to a point between the plug-type connecting parts for the agents and said valve arrangement housing having the light source arranged in line with the intermediate light conductor so that light is conducted from the lamp in the valve arrangement housing through the transition piece for communication with the light conductor of the nozzle.

14. A dental spray handpiece according to claim 1, wherein a switch element for the lamp is disposed on the housing in the region of the switch elements for the agents being sprayed.

15. A dental spray handpiece according to claim 14, wherein the switch element proceeds and is immediately adjacent to the two switch elements for the air and water agents.

16. A dental spray handpiece according to claim 1, wherein said light source is a lamp, the housing contains a valve arrangement for the agents including electrical heating elements, and said lamp receives a supply voltage tapped from the electrical heating elements.

17. A dental spray handpiece according to claim 1, wherein the light source is an incandescent bulb, said incandescent bulb being firmly disposed in a central passage of the nozzle, said nozzle being provided with slip rings connected to said incandescent bulb and engaged by contact springs of the housing so that the source of light and nozzle can rotate relative to the housing of the handpiece.

18. A dental spray handpiece according to claim 17, wherein the connecting element of the nozzle forming the joint means comprises a hollow peg member, said slip rings being disposed as part of said peg member.

19. A dental spray handpiece according to claim 1, wherein said coacting connecting element forming the joint means includes a stepped prong member having a large diameter portion and a small diameter portion and a socket having corresponding large and small diameters for receiving said prong, said light source being an incandescent bulb mounted on the end surface of one of said small diameter prong and small diameter socket with the other of said small diameter prong and socket having an end of the light conductor which extends the length of the nozzle to the discharge orifice.

20. A dental spray handpiece device according to claim 1, wherein said light source comprises a lamp having a design of a cartridge, one of said housing and nozzle having means for releasably holding said cartridge with the light source positioned at the end of the light conductor of said nozzle.

* * * * *